United States Patent
Redl et al.

(10) Patent No.: US 6,852,099 B2
(45) Date of Patent: Feb. 8, 2005

(54) DEVICE FOR CONTROLLABLY APPLYING LIQUIDS TO BODY SURFACES

(75) Inventors: Heinz Redl, Vienna (AT); Zafar Khakpour, Vienna (AT)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 157 days.

(21) Appl. No.: 10/163,201

(22) Filed: Jun. 4, 2002

(65) Prior Publication Data

US 2003/0225380 A1 Dec. 4, 2003

(51) Int. Cl.[7] .............................................. A61M 25/01
(52) U.S. Cl. ......................................... 604/289; 604/82
(58) Field of Search .............................. 604/289, 82–85, 604/518, 519, 65–67, 191, 22–26, 213–216; 222/71, 397, 399; 128/204.22, 202.22

(56) References Cited

U.S. PATENT DOCUMENTS

| | | | | |
|---|---|---|---|---|
| 4,631,055 A | * | 12/1986 | Redl et al. | ..................... 604/82 |
| 5,356,378 A | * | 10/1994 | Doan | ........................ 604/65 |
| 5,582,596 A | * | 12/1996 | Fukunaga et al. | .......... 604/191 |
| 5,616,124 A | * | 4/1997 | Hague et al. | ................. 604/65 |
| 5,648,265 A | | 7/1997 | Epstein | |
| 5,665,067 A | * | 9/1997 | Linder et al. | ................. 604/82 |
| 5,827,223 A | * | 10/1998 | Butterfield | .................... 604/65 |
| 6,063,055 A | | 5/2000 | Epstein et al. | |
| 6,131,572 A | * | 10/2000 | Heinonen | ............... 128/205.24 |
| 6,234,356 B1 | | 5/2001 | Garbasch et al. | |
| 6,371,942 B1 | * | 4/2002 | Schwartz et al. | ........... 604/246 |
| 6,432,084 B1 | | 8/2002 | Levinson et al. | |
| 6,461,361 B1 | | 10/2002 | Epstein | |
| 6,471,667 B1 | | 10/2002 | Epstein | |
| 6,488,650 B1 | | 12/2002 | Epstein et al. | |
| 6,565,539 B1 | * | 5/2003 | Zinger et al. | ............... 604/191 |
| 6,575,940 B1 | | 6/2003 | Levinson et al. | |
| 6,620,125 B1 | | 9/2003 | Redl | |
| 6,651,508 B2 | * | 11/2003 | Baba et al. | ................... 73/754 |
| 2002/0029804 A1 | * | 3/2002 | Liorati et al. | ............... 137/486 |
| 2002/0198564 A1 | | 12/2002 | Pichon et al. | |

FOREIGN PATENT DOCUMENTS

| WO | WO00/09074 A2 | 2/2000 |
|---|---|---|
| WO | WO00/18469 A1 | 4/2000 |

* cited by examiner

Primary Examiner—Larry I. Schwartz
Assistant Examiner—G. Chapman
(74) Attorney, Agent, or Firm—Jeffrey C. Nichols; Bruce M. Center (57) ABSTRACT

A system and method for controllably applying the fluids to a body surface or cavity is disclosed. These fluids can include tissue adhesives, hemostats, sealants, anti-adhesives, or any other fluid capable of being applied to a body surface or cavity. In one embodiment, the system and method is used to apply components of a tissue adhesive with the aid of pressurized gas. This system comprises a tube having a proximal end and a distal end, at least one component lumen and a gas lumen which open at the distal end of the tube, a component source connected to the component lumen, a source of pressurized gas connected to the gas lumen, a sensor capable of delivering a sensor signal, a switch connected to the source of pressurized gas, and a control system programmed to switch off the pressurized gas supply when the sensor signal corresponds to a predetermined limit value.

46 Claims, 10 Drawing Sheets

DEVICE FOR CONTROLLABLY APPLYING LIQUIDS TO BODY SURFACES

FIELD OF THE INVENTION

The invention relates to a device for applying liquids to body surfaces or body cavities. In one embodiment, the invention relates specifically to the application of tissue adhesive components with the assistance of a pressurized gas and a system for controllably applying the tissue adhesive components.

TECHNOLOGICAL BACKGROUND OF THE INVENTION

Devices for applying liquids to body surfaces are known. Devices which apply tissue adhesives using a medicinal gas are disclosed, for example, in EP 146 098 A and its corresponding U.S. Pat. No. 4,631,055 as well as EP 669 100 A and its corresponding U.S. Pat. No. 5,665,067, which are incorporated by reference as if fully set forth herein. A common tissue adhesive is fibrin, which usually comprises a fibrinogen solution, on the one hand, and a thrombin solution, on the other hand, which may be delivered by atomization to the site of application and applied thereto. This spray application may be used for external wound sealing, for example, to stop bleeding from a wound, or to assist in treating burns or skin grafts, and is particularly well suited for sealing wounds within body cavities. For this purpose, a multi-lumen tube or spray catheter may be introduced into the respective body cavity, e.g. by way of minimally invasive surgery, and advanced to a position proximate to the application site. Once positioned, the tissue adhesive may be applied to the application site.

One shortcoming associated with the aforementioned procedure arises when applying the tissue adhesive within a closed body cavity. When applying the tissue adhesive, excessive pressure may be built up within the closed body cavity. Similarly, the open distal end of the catheter may directly contact the inner tissue or organ during use. Both of these problems may result in health-damaging consequences to the patient. It is possible to provide the catheter with optical means, such as a fiber-optic light guide and lenses, and to connect a visualizing device thereto so that the movement of the catheter in the body cavity may be visually checked from the outside. However, this solution is overly complex for many cases and fails to adequately address the safety issues relating to the possible pressure build-up within the closed body cavity or the catheter contacting the tissue.

Therefore, it is an object of the present invention to provide a device and system which avoids the negative consequences of the development of high pressure in the body cavity or of the catheter's contact with body tissue during operation. In particular, the present invention provides safety precautions in the event of a pressure build-up or of the catheter contacting tissue during operation of the device. In addition, the present invention is capable of monitoring pressure within the closed cavity by introducing a flow and/or volume of the pressurized medicinal gas for monitoring the catheter tip and prevent contact with the tissue.

SUMMARY OF THE INVENTION

The present invention relates generally to the application of fluids to a body surface or cavity. These fluids can include tissue adhesives, hemostats, sealants, anti-adhesives, or any other fluid capable of being applied to a body surface or cavity. Much of the following description will address an embodiment wherein a device is used to controllably apply components of a tissue adhesive. It is to be understood, however that the device described can be used to deliver other fluids as stated above.

In one embodiment of the invention, a device for applying the components of a tissue adhesive comprises a multi-lumen tube or catheter. When referring to the tube or catheter the term "distal" will be used to refer to the tip of catheter which is inserted into a patient and the term "proximal" will be used to refer to the end of the catheter which is designed to be outside the body of the patient. The catheter of the present invention has lumens which terminate at the free distal end of the tube, a component delivery device to which the respective lumens of the tube are connected, a source of pressurized gas for supplying a medicinal gas under pressure thereto, a medicinal lumen within the multi-lumen tube and in communication with the pressure gas source, and a sensor capable of providing a sensor signal corresponding to an injection parameter. The sensor may include, without limitation, a contact sensor, a flow sensor, a volume sensor, or a pressure sensor. In particular, the sensor may provide information corresponding to an injection parameter, such as direct or indirect information relating to the pressure in the region of the distal end of the catheter. A switch device is provided for the pressurized gas supply. The switch device is controlled by a control system and may switch off the pressurized gas supply when the sensor signal corresponds to a predetermined limit value. In one embodiment, the pressure at the distal end of the tube or catheter is monitored by a pressure sensor, wherein a first reference value is determined depending on the conditions given, such as, for example, the gas pressure, ambient pressure, or the pressure in the body cavity etc. This first reference value is considered when setting the alarm level. When the alarm level is reached, as detected by the pressure sensor, the gas supply and, thus, the spray application is switched off.

The present invention may include a multi-lumen tube or catheter, which contains at least four lumens therein and which may include a transfer conduit member, positioned near the distal end, to which the pressurized gas source may be connected. The invention may include an adjacent measurement lumen, where the transfer conduit member includes an open annular passage between its outer periphery and an interior wall of the measurement lumen. The measurement lumen freely opens in the direction of the distal end of the multi-lumen tube, whereas the lumen to which the pressurized gas source is connected is sealingly closed around the transfer conduit member. This allows for monitoring of the pressure at a protected site within the catheter tube. Alternate monitoring systems include, without limitation, contact sensors, such as capacitive sensors, conductivity sensors, light sensors or ultrasonic sensors, which are directly attached to the tip of the catheter tube or to the front side of the distal end, thereby enabling the present invention to directly sense tissue contact.

In other embodiments, the pressure monitoring, which may be accomplished directly or indirectly, may be accomplished via a flow measurement or a volume measurement. Electrical lines would not necessarily be required in the catheter tube. An electromechanical pressure transducer may be attached or connected at the rear or proximal end of the catheter tube. The embodiment utilizing an electromechanical pressure transducer includes the aforementioned measurement lumen within the catheter tube. Accordingly, the catheter tube may have four lumens, i.e. two component delivery lumens for separately conveying the two components of the tissue adhesive, a lumen for conveying the pressurized gas, and a measurement lumen. The measuring lumen can communicate with the aforementioned transfer conduit member, and the tube may be provided with a transition region from the pressurized gas lumen to the measurement lumen so that the pressurized gas lumen will be closed at the distal end. The measurement lumen, in its forward-most region, will thereby be an extension of the pressurized gas lumen.

The measurement lumen may have an associated pressure transducer at its proximal end. In an alternate embodiment which uses capacitive sensors or other sensor devices, the measurement lumen may include corresponding electric signal lines towards the proximal end. The proximal end of the catheter tube may be connected to the control system, which may include electronic comparators associated with the sensors. The electronic comparators compare the sensor signal with a stored reference value defining the limit value. The control system may, in particular, comprise an electronic circuit capable of defining this reference value, which may depend on marginal conditions, such as surrounding pressure, pressure within the body cavity, etc.

The controllable switch device for the pressurized gas supply may comprise a solenoid valve which has a control input connected to the control system. Furthermore, a separate switch capable of actuation during operation, for example, a foot switch, may be connected to the control system to initiate operation of the spray application device. However, the operation of the device will be interrupted and the solenoid valve will be closed if the control system and sensors detect that the monitored parameter, e.g. the pressure, reaches the defined limit value or reference value. The control system then actuates the switch device, in particular the solenoid valve, accordingly. In this instance, a display unit as well as an alarm unit which are connected to the control system may additionally be actuated so as to trigger an optical and/or acoustical alarm and to signal to the operating person that either tissue contact or excessive pressure has been detected.

BRIEF DESCRIPTION OF THE DRAWINGS

The invention will hereinafter be described in detail by way of preferred illustrative embodiments and with reference to the drawings. This description is not to be taken in a limiting sense, but is made merely for the purpose of illustrating the general principles of the invention.

DETAILED DESCRIPTION OF THE DRAWINGS

Figures 1, 2, 3:
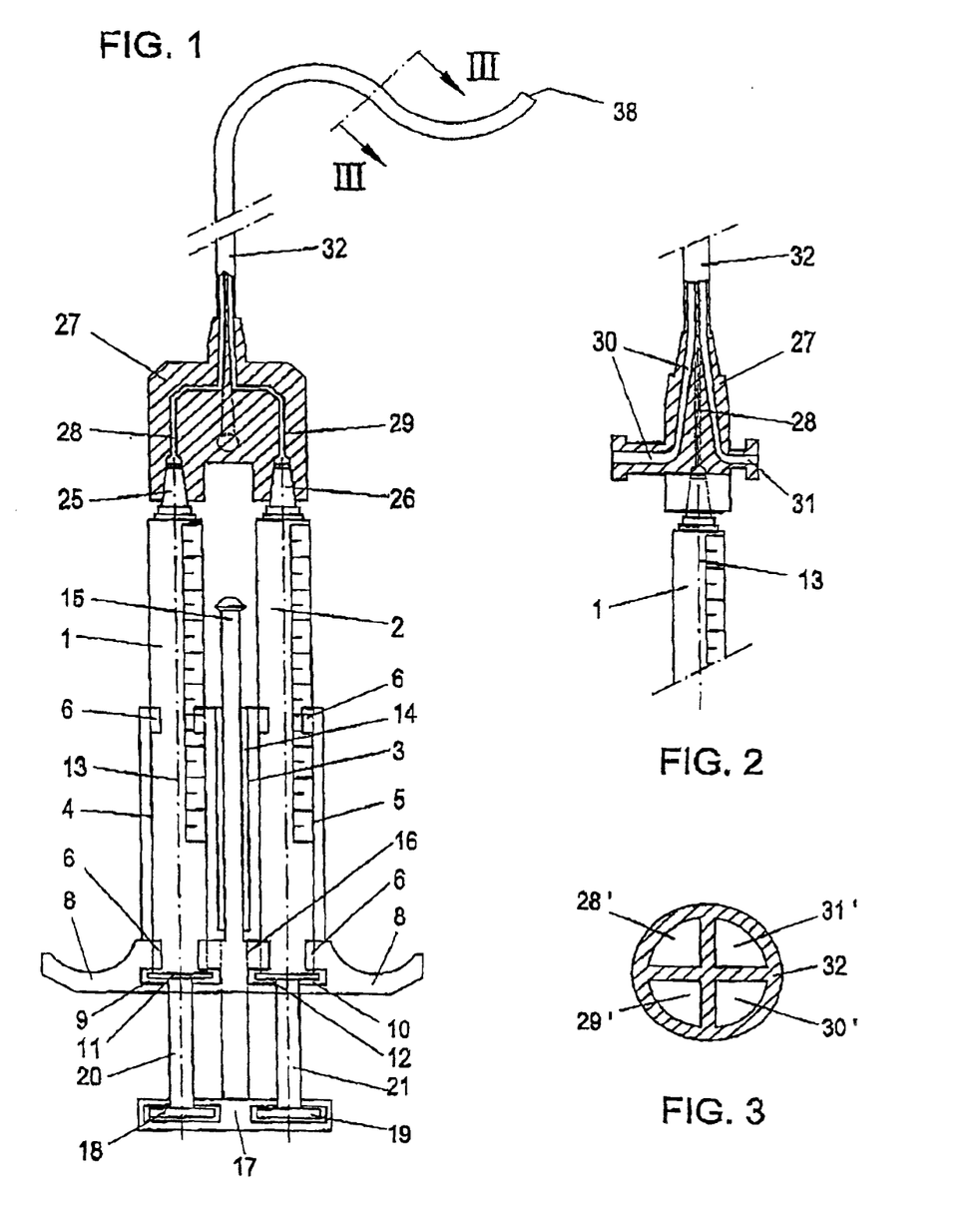
FIG. 1 shows a partially sectioned side view of a tissue adhesive spray application device used in the present invention.
FIG. 2 shows a partial section of this device in a plane at right angles to the sectional plane of FIG. 1.
FIG. 3 shows a cross-section through the catheter tube of the device along line III—III of FIG. 1.

FIGS. 1 to 3 illustrate one embodiment of a conventional dual syringe device attached to a catheter tube 32. As shown, the application device for the components of a tissue adhesive comprises two disposable syringe bodies 1 and 2, one which accommodates a thrombin-containing solution and the other which accommodates a fibrinogen and factor XIII-containing solution. The syringe bodies 1 and 2 are inserted into a holder 3 which has two U-shaped channels 4 and 5. The two U-shaped channels 4 and 5 are provided with latching knobs 6 at the ends thereof, wherein the syringe bodies 1 and 2 engage the latching knobs when inserted into the channels 4 and 5.

At the other end of the holder 3, finger grips 8 are provided which may comprise U-shaped enlargements 9 and 10 in which the flange ends 11 and 12 of the syringe bodies 1 and 2 are received such that the syringe bodies 1 and 2 are fixed in the direction of their longitudinal axes 13.

Between the channels 4 and 5, a gap 14 is provided for a guide rod 15. A penetrating bore 16 may be formed in the holder 3 in the region of the finger grips 8. The guide rod 15 may be connected with a common actuating device 17 for thumb yokes 18 and 19 of the syringe pistons 20 and 21.

Two conical tips 25 and 26 of the syringe bodies 1 and 2 project into appropriately shaped recesses of a connecting head 27 and are connected therewith. Within the connecting head 27, separate conveying channels 28 and 29 lead respectively from each conical tip 25 and 26 to the front side of the connecting head 27. Moreover, a further conveying channel 30 is provided in the connecting head 27 for receiving a medicinal gas, which likewise leads to the front side of the connecting head 27 adjacent the conveying channels 28 and 29. Furthermore, as is illustrated in FIG. 2, a measurement channel 31 may be provided in the connecting head 27 which is located opposite the gas conveying channel 30 and, like the former, is provided with a connecting means for a hose or the like. In an alternate embodiment, the connecting means for the two channels 30 and 31 could also be arranged side by side on the same side of the connecting head 27.

The connecting head 27 may be connected to a four-lumen catheter tube 32. As shown in FIG. 3, the four-lumen catheter may include a first component delivery lumen 28' which is the continuation of the first component conveying channel 28, a second component delivery lumen 29' which is the continuation of the second component conveying channel 29, a gas conveying lumen 30' continuing the gas conveying channel 30, and a measurement lumen 31' which continues the measurement channel 31.

By applying pressure either to the individual pistons 18 and 19, or to the actuating device 17, the components to be mixed are supplied to the site of application.

Depending on the choice of the speed and amount of the medicinal gas applied during the application, the components may be administered in liquid form or in an atomized form.

Figure 4:
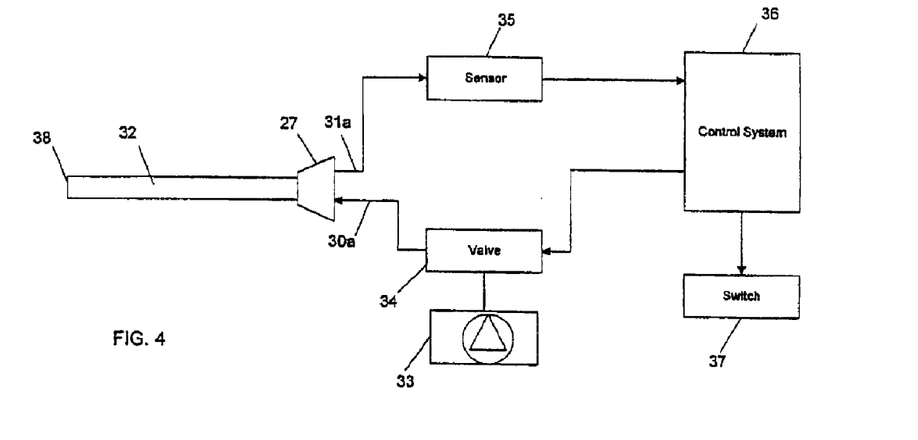
FIG. 4 shows a schematic view of the catheter tube and the pressurized gas supply and monitoring components connected thereto of the present invention.

FIG. 4 shows a schematic diagram of the present invention. As shown, the present invention may comprise a catheter tube 32 which is attached to a connecting head 27, together with the electric components of the device and a source of the medicinal gas. As shown in FIG. 4, the components may include a source of pressurized gas, such as a pump 33, which may be connected via a switch device, for example, a solenoid valve 34, and a hose duct 30a. As shown in FIG. 2, the conveying channel 30 in the connecting head 27 communicates with the catheter tube 32. In particular, conveying channel 30 communicates with gas conveying lumen 30'. The measurement lumen 31' may be connected via the measurement channel 31 in the connecting head 27 (See FIG. 2) and will be in communication with the duct 31a and a sensor 35, for example, a pressure sensor or pressure transducer. The sensor signal obtained at the output of this sensor 35 is supplied to control system 36 which in turn controls the solenoid valve 34 via a control line so as to open or close the solenoid 34. The control system 36 is connected to a foot switch 37 which may be actuated during operation so as to open the solenoid valve 34 and supply pressurized gas from the gas source 33 to the catheter tube 32. Simultaneously, the two tissue adhesive components can be supplied via the first and second component delivery lumens 28' and 29' of the catheter tube 32 (See FIGS. 1 to 3) to the front distal end 38 of the catheter tube 32, thereby resulting in the mixing of the two tissue adhesive components of the tissue adhesive and the spraying of the mixture.

Figure 5:
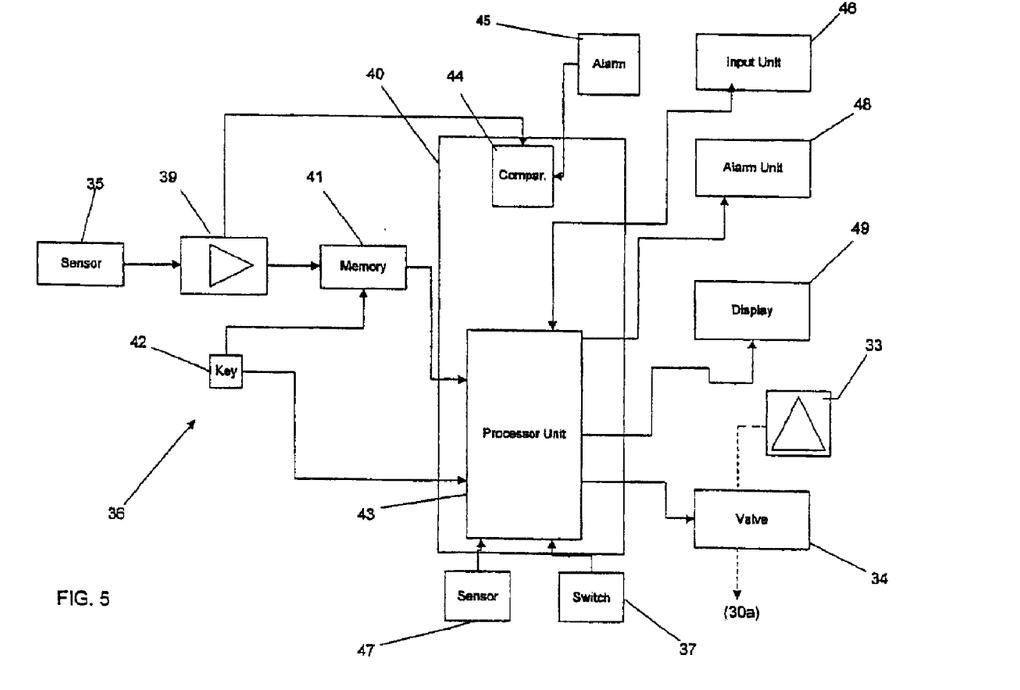
FIG. 5 shows a schematic block diagram of the components of the present invention.

FIG. 5 shows the control system 36 of the present invention in more detail. The sensor signal received from sensor 35 is amplified in a circuit 39. An analog/digital converter may be included when employing digital signal processing architecture. The amplified and, optionally, digitized sensor signal is then applied to a control and monitoring unit 40, where the signal may be amplified. Thereafter, the digitized sensor signal is supplied to a memory 41 which serves as a zero point register for determining the system's zero pressure point (See also FIGS. 15, 16 and 17 explained below). A key 42 is associated with this zero point register 41 so as to fix the zero pressure level of the system and a corresponding output of the key 42 is connected to the control and monitoring unit 40 and, in detail, to a processor unit 43 incorporated therein. Furthermore, the amplified and digitized sensor signal arriving from the circuit 39 is supplied to a comparator 44, which is provided within the control and monitoring unit 40, to which so that it may be compared with a reference value which has been stored as an alarm reference value in an alarm limit register 45. The reference value or limit value is stored in this alarm limit register 45 with the aid of an input unit 46 which is connected to the control and monitoring unit 40 so as to provide a comparable input there.

Figure 12:
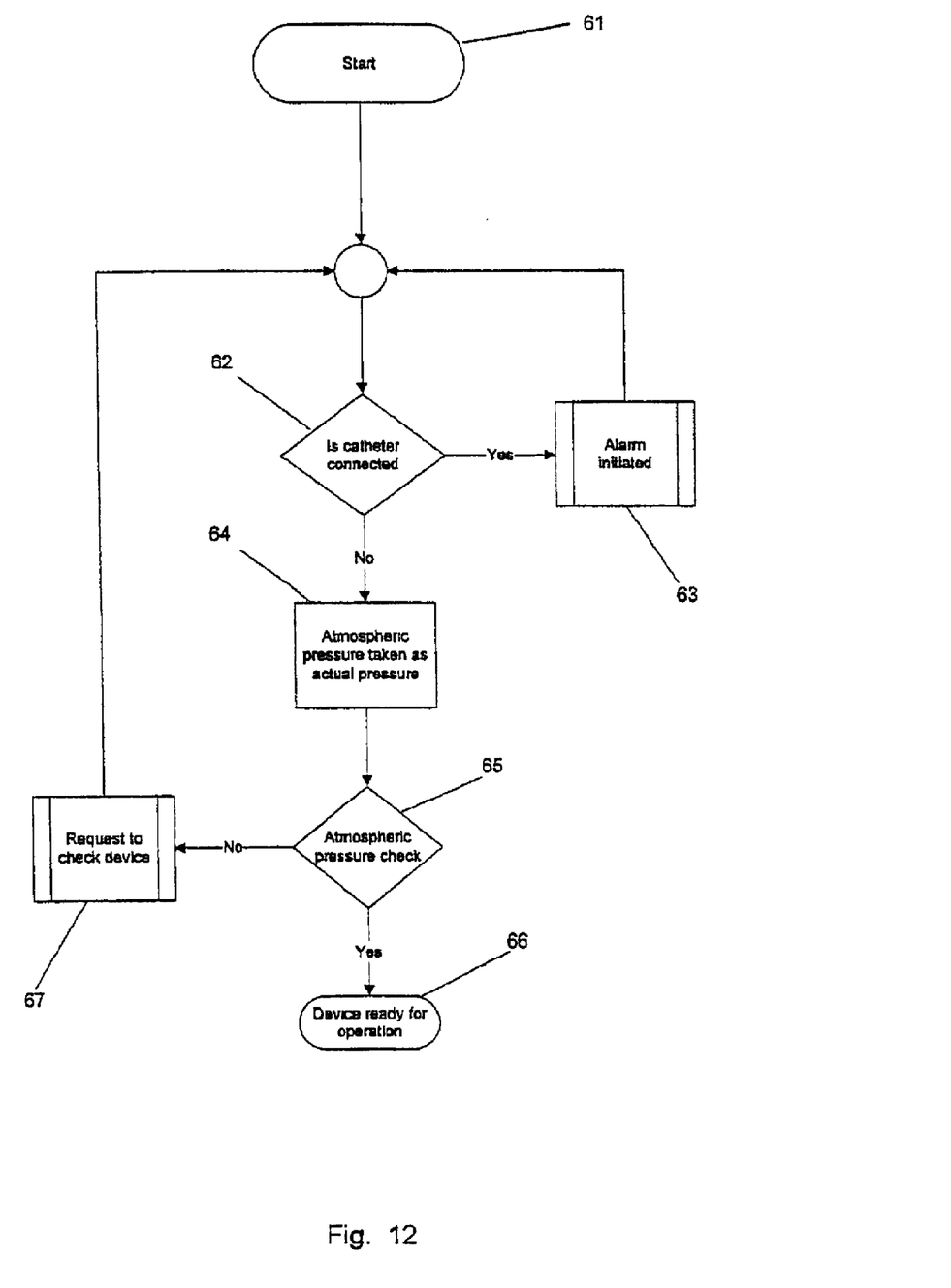
FIG. 12 is a flow chart showing the sequence of controls when switching on the device of the present invention.

In addition to foot switch 37, a sensor 47 may be connected to the processor unit 43 which serves to check the correct connection of the catheter tube 32 in the connecting head 27, and the correct connection of the hose ducts 30a and 31a. Sensor 47 may be an optical sensor, a mechanical sensor, or an inductive sensor. (See the sequences illustrated in FIGS. 12 and 13.) Finally, an alarm unit 48 for delivering an acoustic or optic alarm, a display unit 49, as well as the solenoid valve 34, are connected to the processor unit 43 of the control and monitoring unit 40.

In operation, solenoid valve 34 is opened by means of the foot switch 37 so as to effect a gas supply from the source 33 of pressurized gas to the gas conveying lumen 30' in the catheter tube. However, if sensor 35 detects an inadmissible state during operation, the processor unit 43 causes a movement of the solenoid valve 34 to the off or closed position so that gas under pressure can no longer be provided to the catheter tube 32. For example, in one embodiment utilizing a pressure sensor, the pressure sensor may immediately sense an inadmissible pressure build-up in the region of tip 38 of the catheter tube 32, which is determined by comparing the sensor signal with the reference value in the comparator 44. The processor unit 43 may be designed so that if the inadmissible condition, e.g. an excessive pressure, persists for a short duration and them terminates, the processor unit 43 will automatically move the solenoid valve 34 into the open position again, so long as the foot switch 37 is still pressed down, so that the gas supply can be continued immediately. However, if the inadmissible condition continues for a longer period of time, the gas supply will remain blocked via the solenoid valve 34, so that the cause of the inadmissible condition may be determined and removed before the operation of the device can be continued. It may be provided that following a safety shut-off, as described above, switching on or opening the solenoid valve 34 is only possible after a "reset" input by the user, e.g. by actuating a key (not illustrated), is optionally made after a given time has passed.

Figure 6:
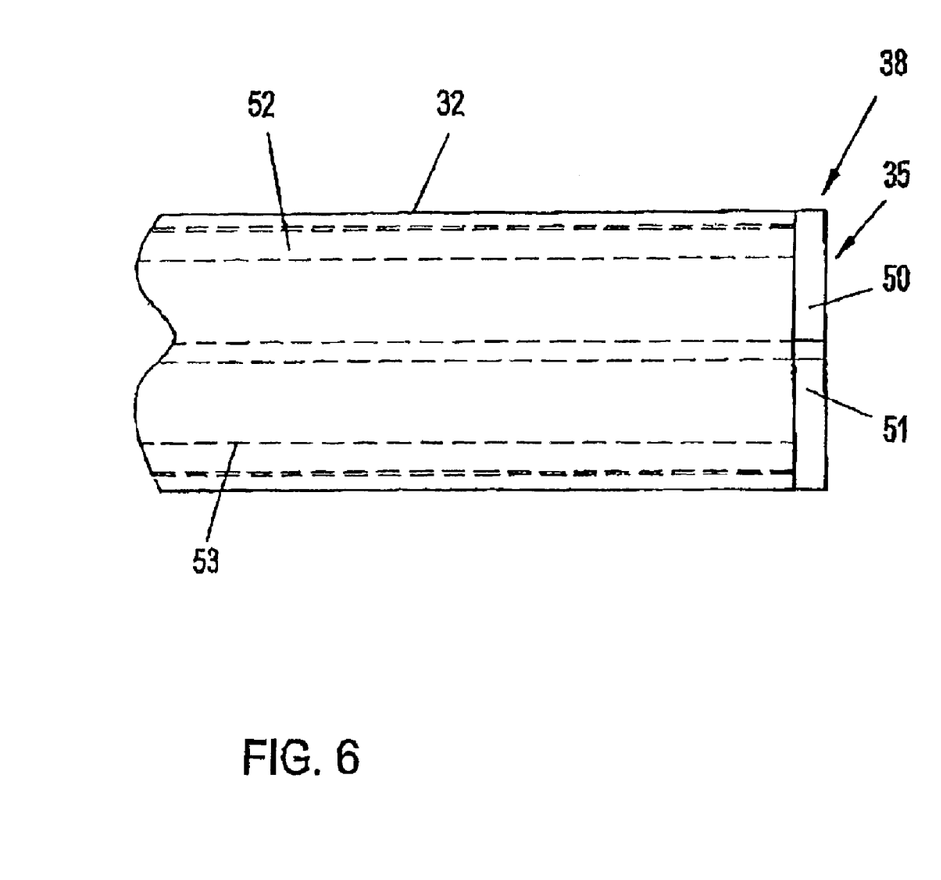
FIG. 6 shows a cross-sectional representation of the front end portion of the catheter tube having a tissue contact sensor attached thereto.
Figure 7:
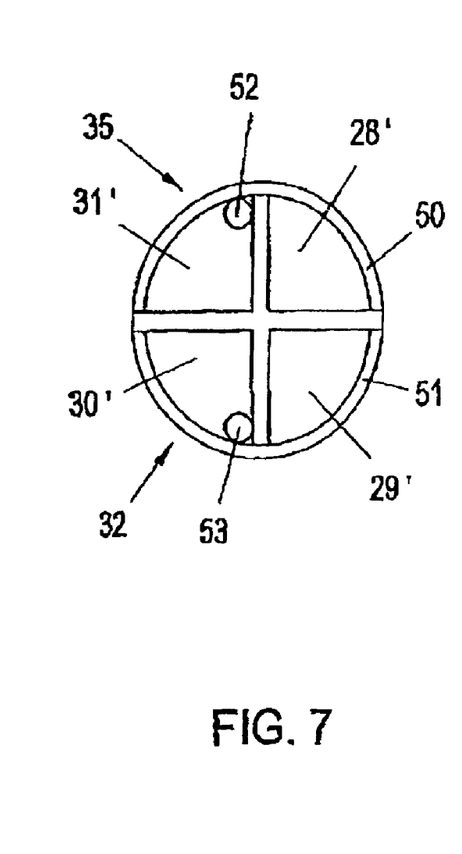
FIG. 7 shows a front end view of the catheter tube of FIG. 6.

In FIGS. 6 and 7, an embodiment of the catheter tube 32 with sensor 35 at its distal end is shown which may optionally be used without the measurement lumen 31'. Sensor 35 may be designed as a contact sensor comprising two conductive, semi-circular sensor electrodes 50 and 51 located separate from each other and to which an electric signal is applied from the electronic circuit 39 (not illustrated in FIGS. 6 and 7). This signal will change upon contact with tissue. The signal change will be supplied to the circuit 39 via signal lines 52 and 53 which may extend along the inner wall of the catheter tube 32 and may be led outwards at the rear, proximal end of the catheter tube 32 via the channel 31 in the connecting head 27.

Figure 8:
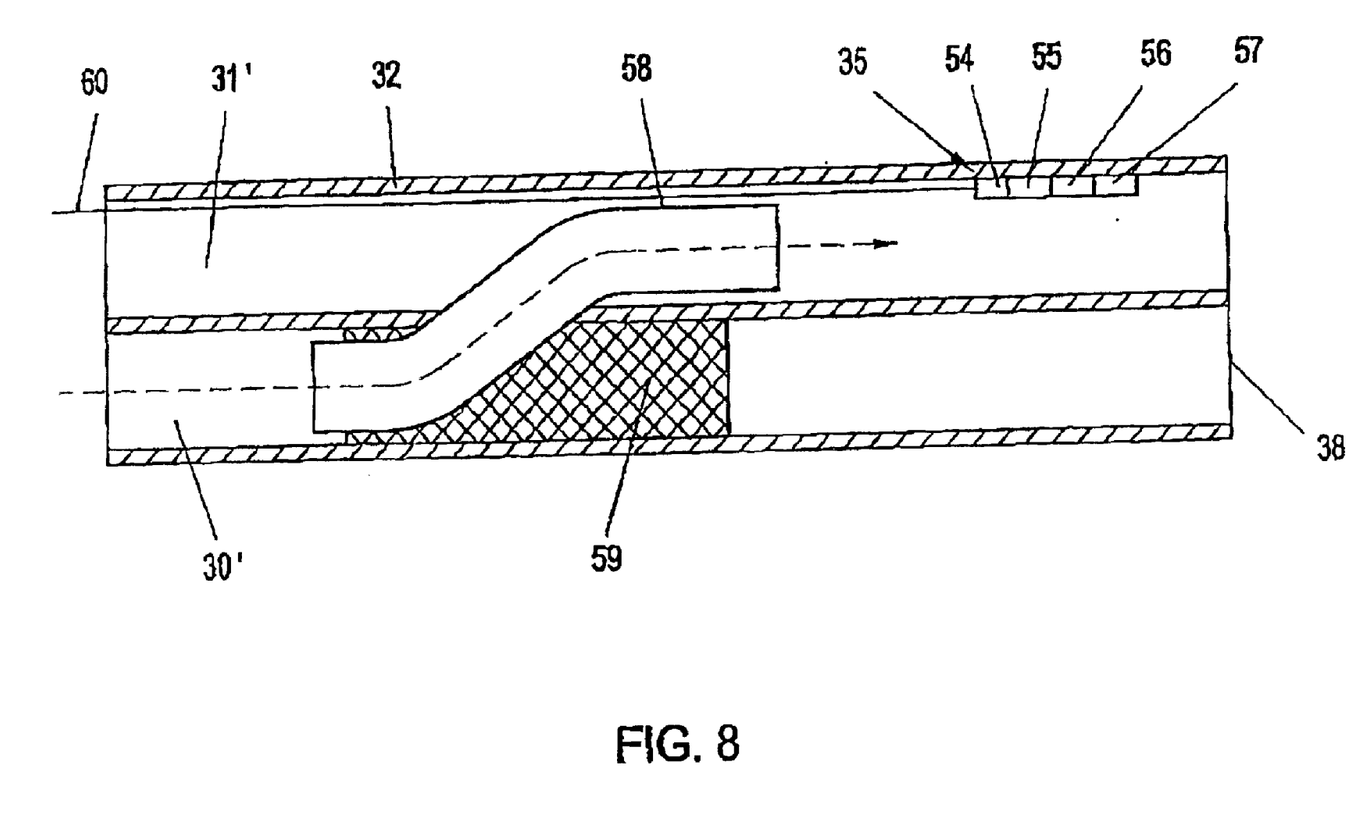
FIG. 8 shows a longitudinal cross-section through the front end portion of a modified catheter tube, comprising a pressurized gas transfer conduit member and a flow sensor in the interior of the catheter tube.

FIG. 8 illustrates the distal region of the catheter tube 32 with a sensor 35 having the form of a flow sensor which is provided in the interior of the measurement lumen 31' at the inner wall thereof. The sensor 35 may be formed in a conventional manner by a combination of several electrodes 54, 55, 56 and 57 successively arranged in the direction of gas flow. (This combined sensor 35 could also be a pressure sensor.) A twice angled (or, alternatively, a straight, obliquely arranged) transfer conduit member 58 having the form of a nozzle-like tube leads from the pressure gas conveying lumen 30' into the measurement lumen 31'. Conduit member 58 may be sealed in the pressure gas conveying lumen 30' by a plastics or adhesive mass 59 so that the pressure gas conveying lumen 30' is sealingly closed at this juncture. In this manner, a defined flow of the pressurized gas past the electrodes 54, 55, 56 and 57 is caused which will depend on the pressure of the pressurized gas, on the one hand, as well as on the counter-pressure from the body cavity (not illustrated) where the front end 38 of the catheter tube 32 is located. If the counter-pressure from the body cavity rises, a progressively lower amount of pressurized gas will be supplied in gas conveying lumen 30', which is determined with the aid of the flow sensor elements 54 to 57 which signal to the control and monitoring unit 40 via a line 60 to trigger the desired safety shut-off.

Figure 9:
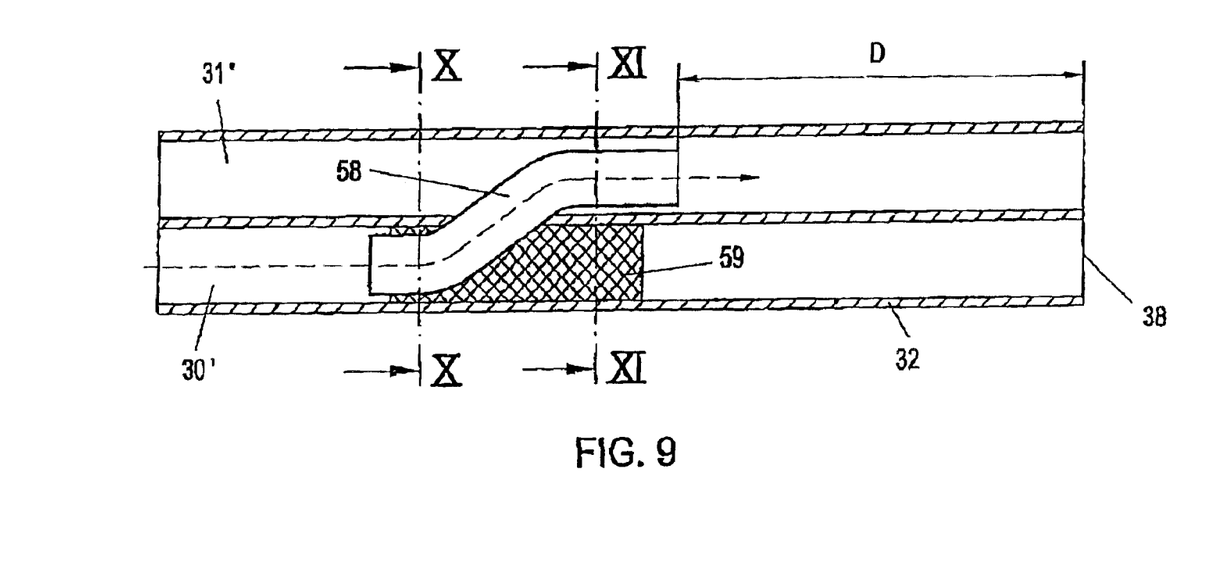
FIG. 9 shows a longitudinal cross-section through an alternate catheter tube, comprising a pressurized gas transfer conduit member in the tube.
Figure 10:
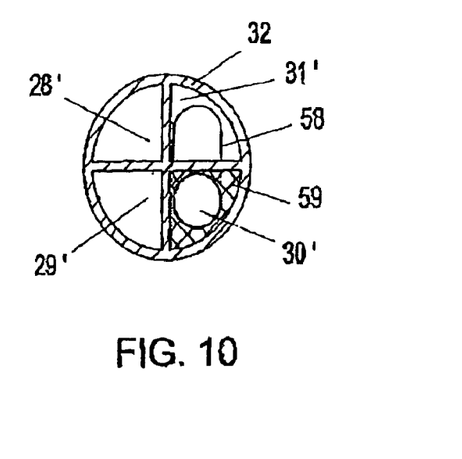
FIG. 10 shows a cross-section of the catheter tube of FIG. 9, taken along lines X—X.
Figure 11:
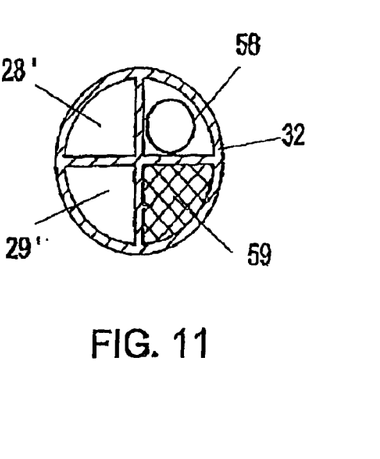
FIG. 11 shows a cross-section of the catheter tube of FIG. 9, taken along lines XI—XI.

FIGS. 9 to 11 illustrate the system of the transfer conduit member 58 in the catheter tube 32 connecting the lumens 30' and 31'. The transfer conduit member 58 may be formed by a nozzle-like metal or plastic tube which is twice angled (or which is straight and obliquely arranged). Conduit member 58 is sealingly inserted in gas conveying lumen 30' wherein the gas is supplied under pressure, by aid of adhesive or plastic stopper 59. The oblique part of conduit member, which is illustrated in FIG. 9, forms a transition to the measurement lumen 31' where it opens into a region located a distance D from the front end 38 of the catheter tube 32. The external diameter of the transfer conduit member 58 is smaller than the cross-section of the measurement lumen 31' so that an annular space remains between the inner wall of the measurement lumen 31' and the outer surface of the transfer conduit member 58. If the medicinal gas is conveyed under pressure through the gas conveying lumen 30', it will emerge at the front end of the mouth of the transfer conduit member 58 and will flow towards the end 38 of the catheter tube where the two components of the tissue adhesive will emerge from the two other lumens 28' and 29' (See FIGS. 10 and 11). The tissue adhesive will be atomized in a manner known to those of skill in the art and will be applied as a spray cone. As the medicinal gas emerges at the front open end of the transfer conduit member 58 under pressure a negative pressure is created therebehind, in particular in the annular space between the outer side of the transfer conduit member 58 and the inner wall of the lumen 31'. This negative pressure propagates rearwardly and can be detected at the rear proximal end of the catheter tube 32, i.e. in the region of the connecting head 27 illustrated in FIG. 1 and in the hose 31a connected thereto and, thus, in sensor 35. To cause this negative pressure which is to be detected by sensor 35, the distance D between the end of the transfer conduit member 58 and the distal front end 38 of the catheter tube 32 is important. Tests have indicated that, in an illustrative embodiment, this distance D may be between 0.5 and 5 cm, in particular between 1 and 2 cm, depending on the cross-sectional size of the catheter tube and of the measurement lumen, respectively. Particularly good results have been obtained in practical tests using conventional spray catheters with the distance D being approximately 1.5 cm. In one illustrative embodiment, the catheter has an outer diameter of 2.3 mm and a measurement lumen size of 0.6 mm. In this embodiment the measurement lumen is 12 mm from the distal tip.

The processor unit 43 of FIG. 5 may comprise a microprocessor or a microcomputer which may assume various control functions when the spray application device is used. For instance, when the device is switched on a checking procedure and a first registering procedure may be run, as is illustrated in the sequence diagram of FIG. 12. Following a starting step 61, block 62 illustrates the step where it is checked whether a catheter tube 32 is connected. This would not be the case when the device is first put into operation, since this could mean that a catheter tube from an earlier use is still connected, which would not be acceptable. Accordingly, for safety reasons, the device should be turned on without a catheter connected thereto. Therefore, if a catheter tube is detected with the aid of the sensor 47 of FIG. 5, the alarm of block 63 is delivered via the alarm unit 48 and a corresponding display is effected via the display unit 49, whereupon it is relayed to the starting point of the process. If a catheter tube 32 is no longer connected, block 64 illustrates the step where the atmospheric pressure sensed by sensor 35 is taken as the actual pressure value. In the next step, illustrated in block 65, the atmospheric pressure is checked via a second independent pressure transducer (not shown) to see whether the pressure sensed by sensor 35 is correct. Block 66 illustrates that the checking process is over and the device is ready to be operated. If, however, as shown in block 65, the assumed pressure does not correspond to the atmospheric pressure, for example, if in the region of the connecting head 27 a fibrin adhesive has agglomerated or there is a production error, it is passed on to block 67 where a request to check the device is made and it is returned to the beginning of the process.

Figure 13:
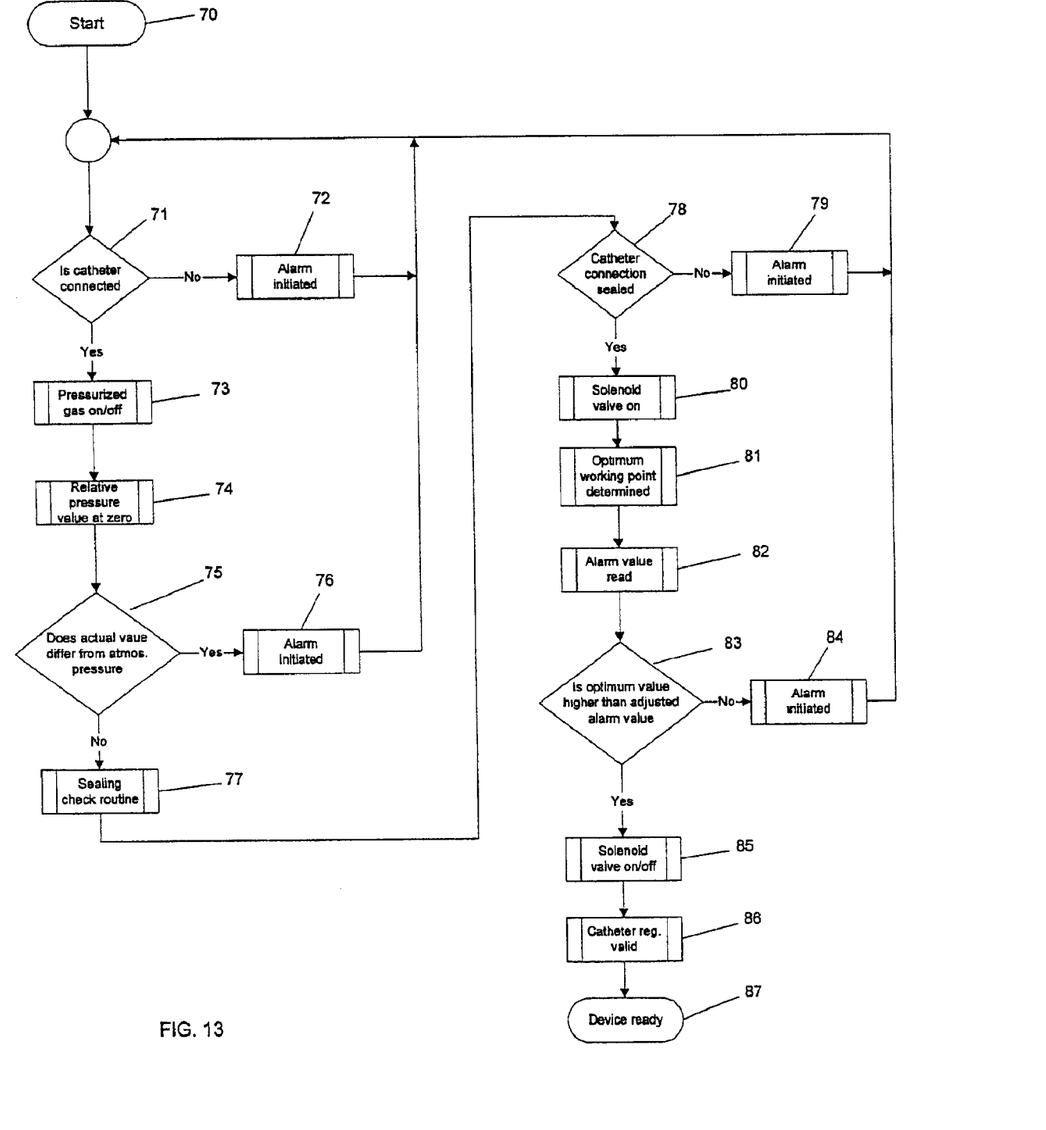
FIG. 13 is a flow chart showing the controls when a new catheter of the present invention is utilized.

If the readiness of the device has been checked in this manner and it has been assured that a new catheter tube 32 is being utilized, this catheter tube will also be calibrated when the device is put into operation. The corresponding calibration process is illustrated in the diagram of FIG. 13. After a first starting step, shown at block 70, the system checks, at a second step shown at block 71, whether the catheter tube 32 has been correctly connected. If the connection is not correct an alarm is delivered, as shown in block 72, and the device is switched off. If, however, the catheter tube 32 has been correctly connected, block 73 illustrates the subsequent step where the pressurized gas is shortly turned on and immediately turned off again. This is done automatically under the control of processor 43 or of the control and monitoring unit 40. The pressure pulse obtained is "sent" through the catheter tube 32, and subsequently, if the catheter tube 32 is all right, the relative pressure value will equal zero. At block 74, the relative pressure is measured and taken as a zero value. Subsequently, at block 75, the system checks to determine whether the actual zero value differs from the atmospheric pressure, i.e. from the pressure value previously calibrated as the zero value. If a difference is detected, block 76 illustrates an alarm signal that is delivered and the device is turned off. As was described with respect to block 72, block 76 relays to the beginning of the process. By repeatedly measuring the atmospheric pressure and repeatedly delivering pressure pulses as described, clogging of the catheter can be prevented and production errors can be detected.

Figure 16:
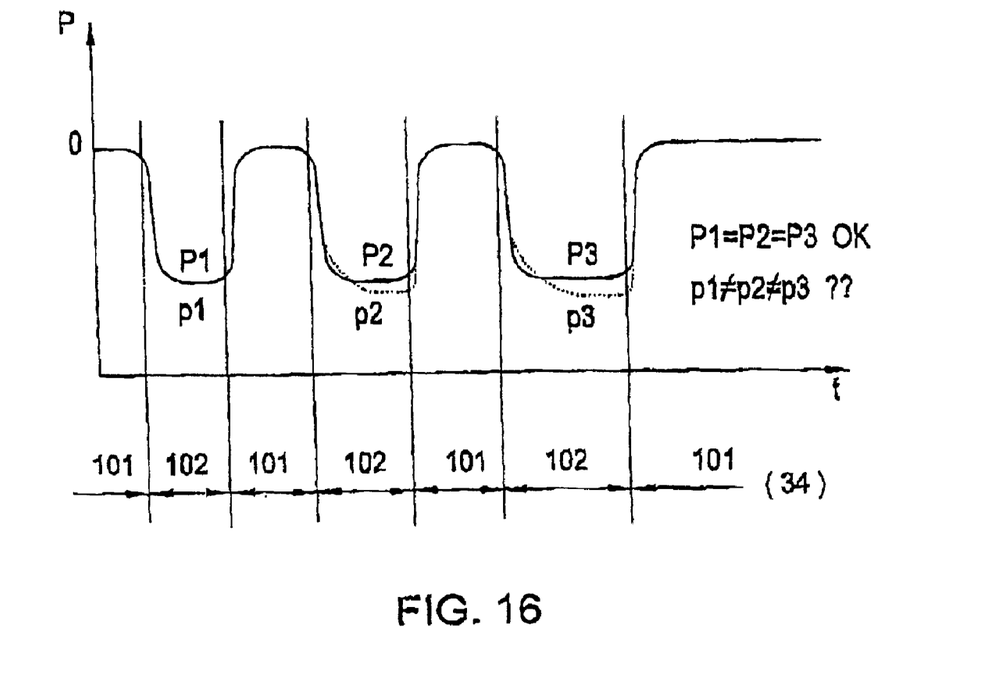
FIG. 16 is a graphical representation of the pressure signal at the measurement lumen of the catheter tube in a leak test outside of the patient in the air.

If the actual zero value in step 75 equals the atmospheric "zero value", block 77 illustrates the performance of a sealing check routine, wherein the solenoid valve 34 is turned on and off and pressure values are taken at predetermined points of time (See FIG. 16).

Block 78 illustrates that if, during this sealing check routine, it is found that the connection of the catheter tube 32 is not tight, the alarm signal of block 79 is delivered, the device is turned off, and it is relayed to the beginning of the process. However, if at the check at block 78 it is found that the catheter tube 32 (including the connecting head 27) is sealingly connected, the solenoid valve 34 is then switched on, as shown at block 80, and, as shown at block 81, the optimum working point of the catheter is determined. In doing so, this optimum working point is obtained with a maximum distance to zero point (See point 103 of FIG. 15). At block 82 the alarm value which has already been adjusted is read in. At block 83 the system checks whether the optimum working point is higher, as an absolute value, than the adjusted alarm value. If the optimum working point is not higher then the adjusted alarm value, as shown at block 84, an alarm signal is delivered and the device is shut off and relayed to the beginning of the process. Otherwise, as shown at block 85, the solenoid valve 34 is turned off again and, as shown at block 86, the initialization of the catheter is registered as valid. At the end of the program process, as shown at block 87, the readiness of the device including the catheter is signaled.

Figure 14:
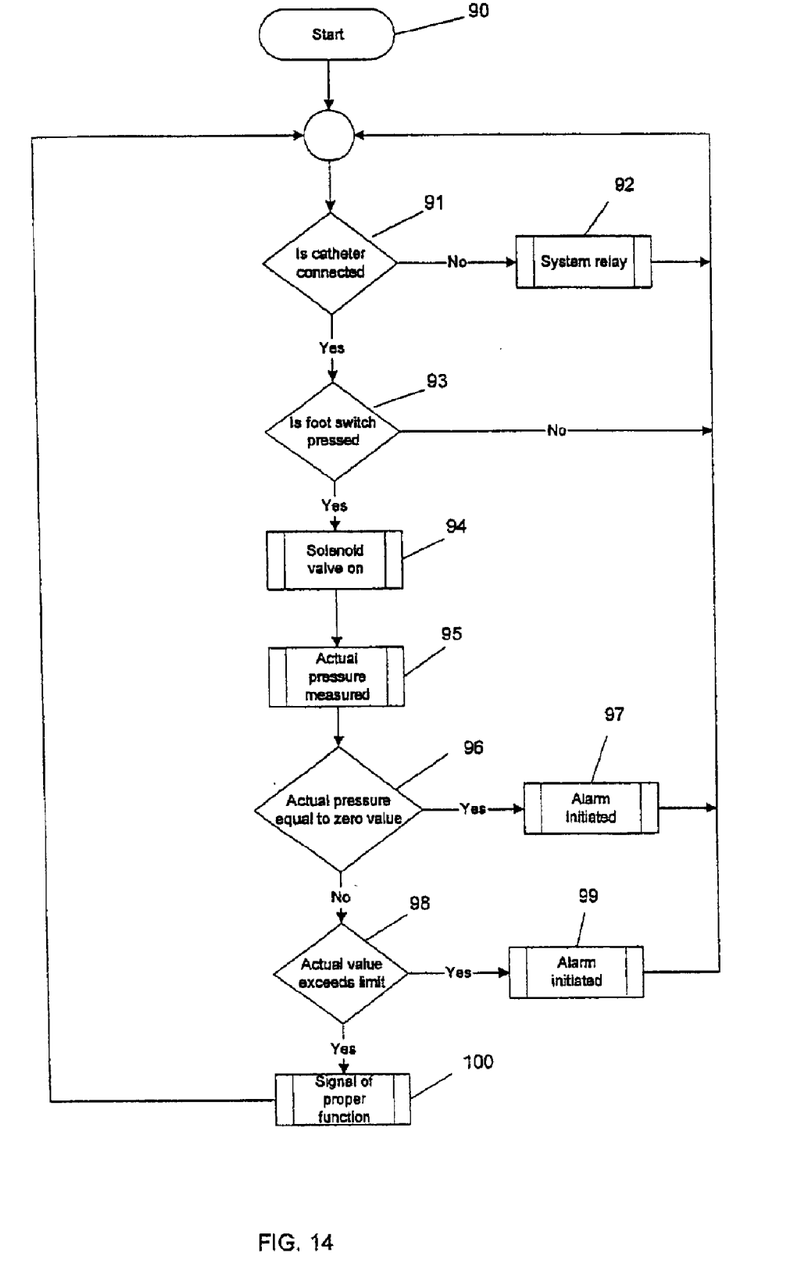
FIG. 14 is a flow chart showing monitoring of the use of the catheter of the present invention.

FIG. 14 illustrates the process control when using the catheter. After a starting step 90, the previously effected initializing is checked for validity at block 91, i.e. the system checks whether a catheter with valid initialization is connected. The system seeks to determine whether the user had changed the working pressure after initialization of the new catheter of FIG. 13, or whether a different catheter has been put into use. If so, operation of the device is blocked, and an alarm signal is delivered. Block 92 of FIG. 14 illustrates the resultant system relay to the beginning of the process. The system then checks, at block 93, to see whether the foot switch 37 is pressed and, if not, the system is relayed to the beginning of the process. If the foot switch 37 is engaged, as shown in block 94, the solenoid valve 34 is turned on so that pressurized gas will be supplied to the catheter tube 32. As shown in block 95, the actual pressure is then measured—by means of the sensor 35—and, as shown at block 96, the system checks to see whether this actual pressure value equals the "zero value" (i.e. the atmospheric pressure). If the pressure values match, then an alarm signal is delivered as shown in block 97 and the device is switched off and the system is relayed to the beginning of the program process. Alternatively, the system is checked at block 98 to determine whether the actual pressure value, obtained after the system is switched on, exceeds the given reference value or limit value, i.e. the alarm threshold. If the alarm threshold is met an alarm is delivered, the device is switched off, and the system is relayed to the beginning of the process. Blocks 96 and 98 check, respectively, whether there has been a possible blocking off of the tip of the catheter tube (check 96), or whether an excessive pressure is already prevailing or a tissue contact is detected (check 98).

If the checking step 98 yields the result that the actual pressure value has not reached the alarm limit value, as shown at block 100, an acoustic and/or optical signal for the proper functioning of the device is delivered. An acoustic signal is particularly viewed as suitable since it can be transmitted immediately to the clinician using the device with the information that the proper function is given (or, for example, that an error has been found), without the clinician having to take his eyes off the patient. The system may also provide for the frequency and/or the volume of the acoustic signal to be dependent on the actual, measured pressure value (e.g., the higher the pressure, the higher, or louder, respectively, the sound).

The cycle illustrated in FIG. 14 when using the device may only take a few milliseconds, such as 100 milliseconds, depending on the actual equipment utilized, and the sequence of the explained steps is repeated in cycles so as to ensure a continuous monitoring of the application device.

Figure 15:
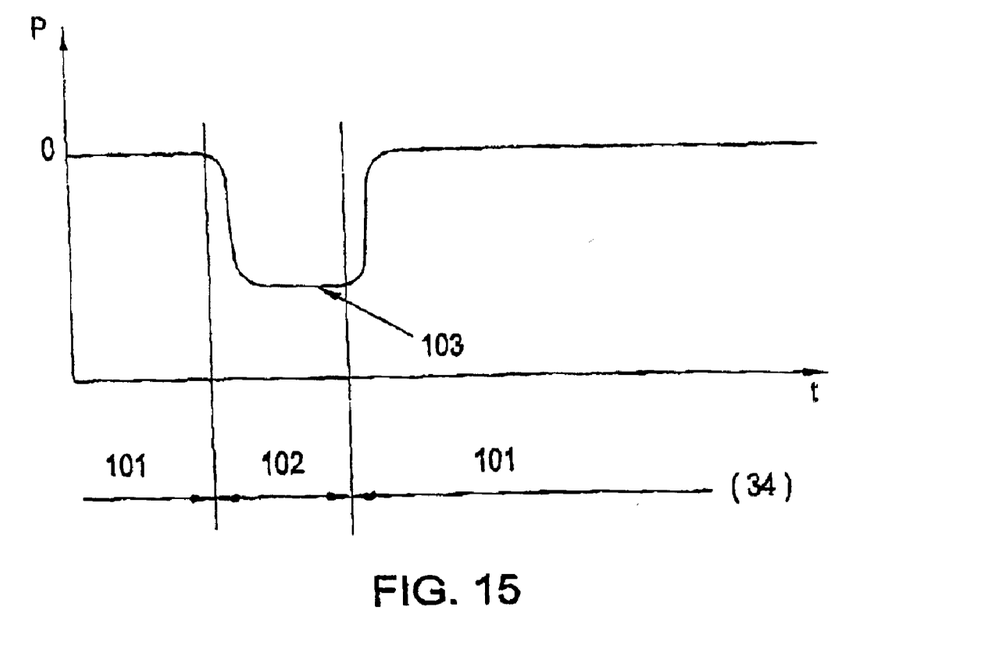
FIG. 15 is a graphical representation of the pressure signal at the measurement lumen of the catheter tube while being switched on and off.

FIG. 15 illustrates the pressure signal as a function of time from the measurement lumen 31' of the catheter tube 32 during the switching on and off of the solenoid valve 34 while the free end 38 of catheter tube 32 still in the air, and if the catheter is all right. The zero value "0" illustrated in FIG. 15 corresponds to the atmospheric pressure or ambient pressure, with this pressure being taken as zero level in the system during the calibration sequence depicted in FIGS. 12 and 13. The lowermost line of FIG. 15 illustrates the on-state 101 and the off-state 102 of the solenoid valve 34. It can be seen that the pressure sensed by the sensor 35, after the solenoid valve 34 is switched on (See line 102), declines relative to the zero value to an optimal working point 103, which results if there is no counter-pressure at the distal end 38 of the catheter tube 32. This optimum working point 103 is typically in the range of 0–40 mmHg. In the case of a defective catheter, on the other hand, the measured pressure would be above value 103 when the solenoid valve is switched on at 102, and could possibly be above the zero level of the system.

FIG. 16 is a graphical representation of the sealing test mentioned in connection with step 77 of FIG. 13, in the air, with pressure P shown as a function of time t. As with FIG. 15, respective on-states 102 and off-states 101 of the solenoid valve 34 are schematically shown in the lower line in the diagram. If the same pressure values P1=P2=P3 are measured during repeated switching on and off, in particular at the maximum or optimum working point (region 103 in FIG. 15), the catheter device is all right and ready for use. If during this repeated switching on and off it is determined that the pressure values $p_1 \neq p_2 \neq p_3$ are different, particularly if they become progressively more negative (with the absolute value increasing), this would suggest a leak in the system. This is signaled at block 79 in FIG. 13, and it is relayed to the beginning of the process.

Figure 17:
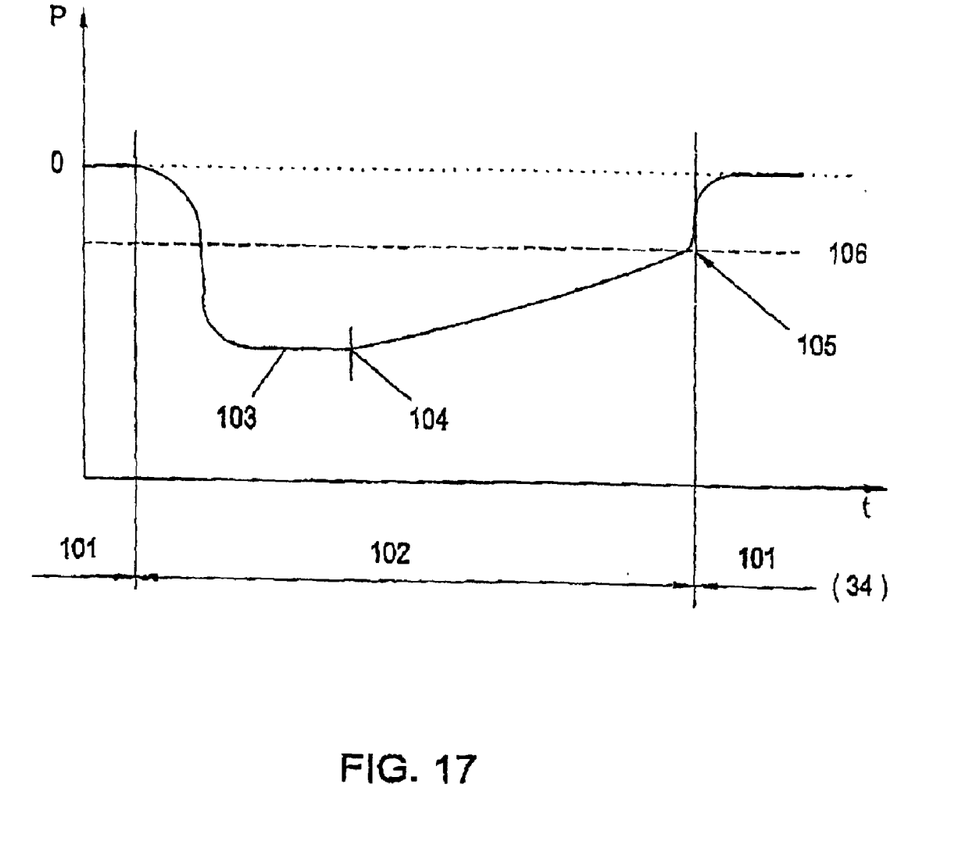
FIG. 17 is a graphical representation of the pressure signal at the measurement lumen of the catheter tube in a test case with a sudden pressure increase which was simulated by dipping the catheter end into a water-filled measuring flask.

Finally, FIG. 17 illustrates an exemplary sequence of the pressure signal, or of the sensor signal, (pressure P at the measurement lumen 31' of the catheter tube 32), where, at a point in time 104 after the solenoid valve 34 has been switched on, the catheter tube tip 38 is, for example, immersed in a water-filled measuring flask. Pressure P then will rise from the working point 103 until, at point of time 105, it has reached the set limit value or reference value 106, i.e. the alarm limit. If this state, shown as step 98 in FIG. 14, has been detected, the safety shut-down of step 99 in FIG. 14 will follow, with the pressure P again returning to the adjusted zero level of the system. The safety threshold or alarm limit value 106, may, for example, be determined at 0.1 bar negative pressure.

The system is designed such that after the solenoid valve 34 has been switched on the pressure sequence shown in FIGS. 15, 16 and 17 will pass the threshold value 106 from above, where the solenoid valve 34 will remain open, as it will be switched off only during a positive increase of the pressure signal, so that the pressure sensed by sensor 35 equals the limit value 106. When using the device, if there is a spray application of the tissue adhesive in a body cavity and the pressure in the body cavity is somewhat higher than the ambient pressure, during the proper functioning of the system a pressure signal will adjust between the two levels 103 and 106.

As discussed above, the distance D from the open end of the transfer conduit member 58 to the catheter end 38 is important for the negative pressure formation in the measurement lumen 31'. For example, distance D must not be too long or else the negative pressure to be measured will not be produced, as compared to the ambient pressure, and an overpressure will be formed. The maximum negative pressure (level 103) results when the pressurized gas is freely released into the environment (See FIG. 15).

The invention is not limited to the previously described example which, at present, is considered to be the preferred embodiment, but further changes and modifications are possible within the scope of the invention. For example, the present invention can be used to apply a variety of fluids to a body surface or cavity, including tissue adhesives, hemostats, sealants, or anti-adhesives. Furthermore, electronic sensors may be used in the region of the catheter tip 38, as illustrated by way of example in FIGS. 6 and 7, or 8. However, since such sensors in the region of the catheter tip require a separate signal line extending through the catheter the previously described pressure or flow measurement techniques are considered particularly advantageous.

What is claimed is:

1. A system for controllably applying one or more fluid components with the aid of pressurized gas, the system comprising:
   a tube having a proximal end and a distal end, the tube having at least one component lumen and a gas lumen which open at the distal end of the tube;
   a component source connected to the at least one component lumen;
   a source of pressurized gas connected to the gas lumen;
   a contact sensor at the distal end of the tube, the contact sensor capable of delivering a sensor signal;
   a switch connected to the source of pressurized gas; and
   a control system communicating with the contact sensor via the sensor signal and communicating with the switch, wherein the control system is programmed to switch off the pressurized gas supply when the sensor signal corresponds to a predetermined limit value.

2. The system of claim 1, wherein the contact sensor is selected from the group consisting of a capacitive sensor, a conductivity sensor, a light sensor and an ultrasonic sensor.

3. The system of claim 2, wherein the contact sensor is a semiconductor sensor.

4. The system to claim 1, wherein the control system comprises an electronic comparator capable of comparing the sensor signal with a reference value defining the predetermined limit value.

5. The system of claim 4, wherein the control system comprises means for determining the reference value.

6. The system of claim 1, wherein an alarm unit is connected to the control system and the control system is programmed to activate the alarm unit upon correspondence of the sensor signal with the predetermined limit value.

7. The system of claim 1, wherein the switch comprises a solenoid valve which has a control input connected to the control system.

8. The system of claim 1, wherein the one or more fluid components comprise one or more components of a tissue adhesive.

9. The system of claim 1, wherein the one or more fluid components is selected from the group consisting of tissue adhesives, hemostats, sealants, anti-adhesives.

10. A system for controllably applying one or more fluid components with the aid of pressurized gas, the system comprising:
    a tube having a proximal end and a distal end, the tube having at least one component lumen, a measurement lumen, and a gas lumen which open at the distal end of the tube;
    a component source connected to the at least one component lumen;
    a source of pressurized gas connected to the gas lumen;
    a flow indicating sensor within the measurement lumen, the flow indicating sensor capable of delivering a sensor signal;
    a switch connected to the source of pressurized gas; and
    a control system communicating with the flow indicating sensor via the sensor signal and communicating with the switch, wherein the control system is programmed to switch off the pressurized gas supply when the sensor signal corresponds to a predetermined limit value.

11. The system of claim 10 further comprising a transfer conduit arranged near the distal end of the tube, wherein the transfer conduit connects the gas lumen to the measurement lumen.

12. The system of claim 11 wherein the transfer conduit has a proximal end in communication with the gas lumen and a distal end in communication with the measurement lumen, and wherein the gas lumen is sealingly closed around the transfer conduit at the proximal end and the distal end of the transfer conduit is contained within the measurement lumen creating an annular region therebetween and wherein the transfer conduit opens freely in the direction of the distal end of the tube.

13. The system of claim 12, wherein the transfer conduit member is a nozzle tube.

14. The system of claim 12, wherein the distal end of the transfer conduit opens within the measurement lumen at a distance of 0.5 to 5 cm from the distal end of the tube.

15. The system of claim 14, wherein the distal end of the transfer conduit opens within the measurement lumen at a distance of 1 to 2 cm from the distal end of the tube.

16. The system of claim 14, wherein the distal end of the transfer conduit opens within the measurement lumen at a distance of approximately 1.5 cm from the distal end of the tube.

17. The system of any one of claims 12 to 16, wherein the tube has a pressure sensor connected to the measurement lumen proximal end of the tube.

18. The system of claim 12 wherein the flow indicating sensor is proximate the transfer tube and is capable of measuring negative pressure which is indicative of flow.

19. A method for controllably applying one or more fluid components with the aid of pressurized gas, the method comprising the steps of:
    delivering the one or more components through a multi-lumen tube;
    delivering pressurized gas to the multi-lumen tube;
    sensing pressure within one of the lumens of the multi-lumen tube; and
    switching off the pressurized gas if the sensed pressure reaches a predetermined value.

20. The method of claim 19 wherein the sensing pressure step further comprises the step of sensing pressure for at least a predetermined duration and the step of switching off the pressurized gas is undertaken if the sensed pressure reaches the predetermined value for the predetermined duration.

21. The method of claim 19 further comprising the additional step of continuing to sense pressure in distal region of the multi-lumen tube and switching on the pressurized gas if the sensed pressure drops below the predetermined value within a predetermined duration.

22. The method of claim 19, wherein the one or more fluid components comprise one or more components of a tissue adhesive.

23. The method of claim 19, wherein the one or more fluid components is selected from the group consisting of tissue adhesives, hemostats, sealants, anti-adhesives.

24. The method of claim 19 wherein the step of sensing pressure comprises sensing pressure in the distal region of the lumen of the multi-lumen tube.

25. The method of claim 19 wherein the step of sensing pressure comprises sensing pressure in the proximal region of the lumen of the multi-lumen tube.

26. The system of claim 10 wherein the flow indicating sensor comprises a plurality of electrodes successively arranged in the direction of gas flow at the distal end of the measurement lumen.

27. The system of claim 10 wherein the flow indicating sensor comprises a pressure sensor at the distal end of the measurement lumen.

28. The system of claim 10 wherein the flow indicating sensor comprises an electromechanical pressure transducer at the proximal end of the measurement lumen.

29. The system to claim 10, wherein the control system comprises an electronic comparator capable of comparing the sensor signal with a reference value defining the predetermined limit value.

30. The system of claim 29, wherein the control system comprises means for determining the reference value.

31. The system of claim 10, wherein an alarm unit is connected to the control system and the control system is programmed to activate the alarm unit upon correspondence of the sensor signal with the predetermined limit value.

32. The system of claim 10, wherein the switch comprises a solenoid valve which has a control input connected to the control system.

33. The system of claim 10, wherein the one or more fluid components comprise one or more components of a tissue adhesive.

34. The system of claim 10, wherein the one or more fluid components is selected from the group consisting of tissue adhesives, hemostats, sealants, anti-adhesives.

35. A method for controllably applying one or more fluid components with the aid of pressurized gas, the method comprising the steps of:
delivering the one or more components through a multi-lumen tube;
delivering pressurized gas to the multi-lumen tube;
sensing flow within one of the lumens of the multi-lumen tube; and
switching off the pressurized gas if the sensed flow reaches a predetermined value.

36. A system for controllably applying one or more fluid components with the aid of pressurized gas, the system comprising:
a tube having a proximal end and a distal end, the tube having at least one component lumen, a measurement lumen, and a gas lumen which open at the distal end of the tube;
a transfer conduit arranged near the distal end of the tube, wherein the transfer conduit connects the gas lumen to the measurement lumen;
a component source connected to the at least one component lumen;
a source of pressurized gas connected to the gas lumen;
a sensor capable of delivering a sensor signal;
a switch connected to the source of pressurized gas; and
a control system communicating with the sensor via the sensor signal and communicating with the switch, wherein the control system is programmed to switch off the pressurized gas supply when the sensor signal corresponds to a predetermined limit value.

37. A system for controllably applying one or more fluid components with the aid of pressurized gas, the system comprising:
a tube having a proximal end and a distal end, the tube having at least one component lumen and a gas lumen which open at the distal end of the tube;
a component source connected to the at least one component lumen;
a source of pressurized gas connected to the gas lumen;
a flow indicating sensor at the distal end of the tube and in contact with the flowing gas, the flow indicating sensor capable of delivering a sensor signal;
a switch connected to the source of pressurized gas; and
a control system communicating with the flow indicating sensor via the sensor signal and communicating with the switch, wherein the control system is programmed to switch off the pressurized gas supply when the sensor signal corresponds to a predetermined limit value.

38. The system of claim 37 wherein the flow indicating sensor comprises a plurality of electrodes successively arranged in the direction of gas flow at the distal end of the tube.

39. The system of claim 37 wherein the flow indicating sensor comprises a pressure sensor at the distal end of the tube.

40. The system to claim 37, wherein the control system comprises an electronic comparator capable of comparing the sensor signal with a reference value defining the predetermined limit value.

41. The system of claim 40, wherein the control system comprises means for determining the reference value.

42. The system of claim 37, wherein an alarm unit is connected to the control system and the control system is programmed to activate the alarm unit upon correspondence of the sensor signal with the predetermined limit value.

43. The system of claim 37, wherein the switch comprises a solenoid valve which has a control input connected to the control system.

44. The system of claim 37, wherein the one or more fluid components comprise one or more components of a tissue adhesive.

45. The system of claim 37, wherein the one or more fluid components is selected from the group consisting of tissue adhesives, hemostats, sealants, anti-adhesives.

46. A method for controllably applying one or more components of a tissue adhesive with the aid of pressurized gas, the method comprising the steps of:
calibrating the multi-lumen tube by sending a pressure pulse through the tube and sensing the pressure in the distal region of the multi-lumen tube;
delivering the one or more components through at the multi-lumen tube;
delivering pressurized gas to the multi-lumen tube;
sensing pressure in the distal region of the multi-lumen tube;
comparing the sensed pressure with a predetermined limit value; and
switching off the pressurized gas if the sensed pressure reaches the predetermined limit value.

* * * * *